United States Patent [19]

Williams

[11] 4,058,594

[45] Nov. 15, 1977

[54] IMMUNO-SUPPRESSIVE AGENTS

[76] Inventor: John Williams, 30 Hornby Drive, Nantwich, Cheshire, CW5 6JP, England

[21] Appl. No.: 713,242

[22] Filed: Aug. 10, 1976

Related U.S. Application Data

[62] Division of Ser. No. 535,143, Dec. 20, 1974, Pat. No. 3,993,775.

[30] Foreign Application Priority Data

Apr. 25, 1974 United Kingdom ............... 18226/74

[51] Int. Cl.$^2$ ...................... A61K 9/40; A61K 35/78; A61K 31/23; A61K 31/20
[52] U.S. Cl. .................................... 424/37; 424/195; 424/312; 424/318
[58] Field of Search .................. 424/195, 318, 312, 37

[56] References Cited

FOREIGN PATENT DOCUMENTS 1,240,513  7/1971  United Kingdom
1,082,624  5/1965  United Kingdom

OTHER PUBLICATIONS

E. F. Steinmetz, "Codex Vegelabilis", item 768.
Millar et al, British Medical Journal, Mar. 31, 1973, pp. 765–768.
Field et al, British Medical Journal, Dec. 22, 1973, one page.
The Lancet, Nov. 10, 1973 p. 1080.

*Primary Examiner*—Donald B. Moyer
*Attorney, Agent, or Firm*—Bacon & Thomas

[57] ABSTRACT

A method of providing an immuno-suppressive effect in the control or prophylaxis of neurological disorders, such as multiple sclerosis, and in organ and tissue transplants comprising administering a daily dosage of 5mg to 3g of γ-linolenic or dihomo-γ-linolenic acid or a functional derivative thereof, optionally together with a daily dosage of 25mg to 3g of linoleic acid or a functional derivative thereof. An oil extract from seeds of *Oenothera biennis L.* is a convenient source of γ-linolenic acid and linoleic acid.

8 Claims, 1 Drawing Figure

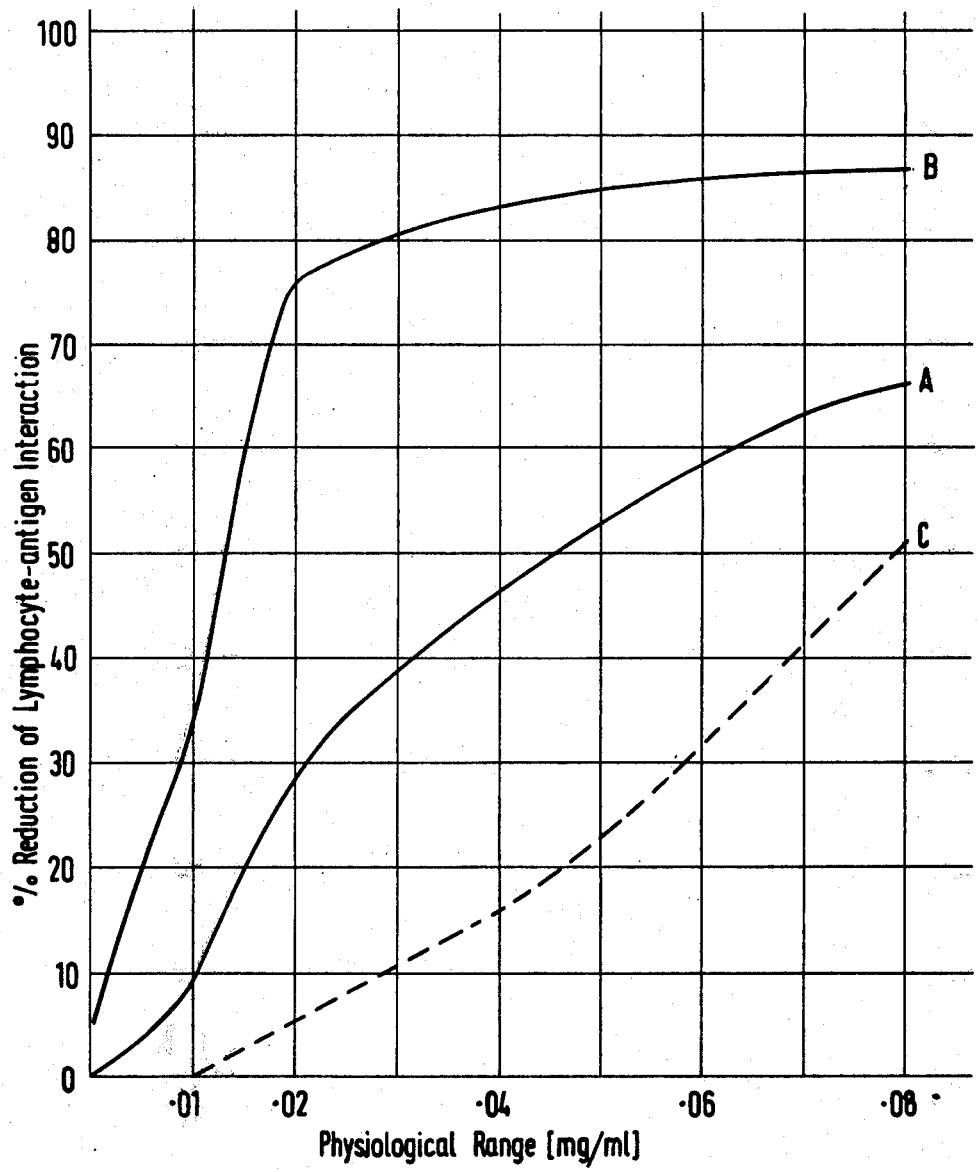

IMMUNO-SUPPRESSIVE AGENTS

This is a division, of application Ser. No. 535,143, filed Dec. 20, 1974 now U.S. Pat. No. 3,993,775.

BACKGROUND OF THE INVENTION

The present invention relates to immunosuppressive agents for the control or prophylaxis of neurological disorders such as multiple sclerosis, and for use in the field of organ and other tissue transplants.

It has been established that administration of linoleic acid (9,12-octadecadienoic acid) has an immunosuppressive effect on the lymphocyte-antigen reaction which has a destructive effect on the protective myelin sheath of the nervous system and is believed to be the factor responsible for relapses in multiple sclerosis. Large doses of vegetable oils rich in linoleic acid such as sunflower oil and safflower oil have been administered to subjects suffering from multiple sclerosis and it has been found that this treatment does lead to a reduction in the frequency and severity of relapses.

However it is thought that the consumption of large doses (for example 4 tablespoons) of vegetable oil daily over a prolonged period, frequently for several years, can lead to undesirable side effects. Firstly the swallowing of large quantities of oil can produce nausea. Secondly a large intake of linoleic acid can give rise to high levels of linoleic acid in the blood-stream where it is susceptible to auto-oxidation with the formation of peroxides and possible combination with free radicals to form toxic products. Finally vegetable oils such as sunflower oil and safflower oil contains a varying content of linolenic acid (9,12,15-octadecatrienoic acid) which, if the daily intake reaches 0.1% of the total dietary calories, can block the normal metabolic elongation of linoleate to arachidonate (5,8,11,14-eicosatetraenoate), the latter being an important component of the myelin sheath.

There is thus a need for a new treatment for multiple sclerosis which avoids the necessity for the consumption of large quantities of vegetable oils containing high levels of linoleates but which serves to maintain an adequate level of arachidonates in the body.

There is also a need for immuno-suppressive agents for use in the control or prophylaxis of neurological disorders generally and in the transplanting of organs and other tissues from a donor to a recipient patient. Thus the control of various stages of the immune response is of major importance in transplantation of organs and other tissues.

British Patent Specification No. 896,903 (Calmic Ltd). describes and claims pharmaceutical compositions containing linoleic acid and arachidonic acid for use in the prevention and treatment of atheromic conditions and in particular atherosclerosis. Although the mode of action of arachidonic acid is not known, it has been found that arachidonic acid lowers the cholesterol level in the blood, a high blood cholesterol level being a symptom of atherosclerosis.

British Patent Specification No. 1,802,624 (Calmic Ltd.) discloses the effectiveness of γ-linolenic acid (6,9,12-octadecatrienoic acid) in the treatment of vascular diseases and claims therapeutic compositions containing γ-linolenic acid and its derivatives and in particular an oil extracted from the seeds of the Evening Primrose (*Oenothera biennis L.*) which is rich in the triglyceride of γ-linolenic acid. It is known that γ-linolenic acid is an important intermediate in the metabolism of linoleic acid to arachidonic acid and it has been found that while only a part of any linoleic acid which is administered is converted to arachidonic acid, almost all γ-linolenic acid administered to living tissue is rapidly converted to arachidonic acid. It has further been found that during the onset of illness which is accompanied by abnormal lipid metabolism the conversion of linoleic acid to γ-linolenic acid is inhibited and this is thought to be a factor in the fall of the arachidonic acid level.

British Patent Specification No. 1,240,513 (Ono Pharmaceutical Co., Ltd.) describes and claims therapeutic compositions for the treatment of atherosclerosis containing as active ingredient at least 30% by weight of the methyl or ethyl ester of γ-linolenic acid. A process for the preparation of the compositions is described which comprises up-grading the γ-linolenic acid content of seed oil extracted from seeds of the *Oenothera* species (which normally contains about 7 to 26% of γ-linolenic acid) by treatment with urea.

DESCRIPTION OF THE INVENTION

It has been discovered that γ-linolenic acid itself, functional derivatives of γ-linolenic acid and oil extracts from seeds such as those of the *Oenothera* and *Borago Officinalis* species containing γ-linolenic acid or functional derivatives thereof, have a much greater immunosuppressive effect on lymphocyte and phagocyte activity than do pure linoleic acid and the linoleates.

Thus according to the invention there is provided a method of providing an immuno-suppressive effect in the control or prophylaxis of neurological disorders such as multiple sclerosis and in organ and tissue transplants, which method comprises administering a daily dosage of from 5mg or 3g of γ-linolenic acid or a functional derivative thereof, for example the $C_1$–$C_4$ alkyl (e.g. methyl and ethyl) esters and the glycerides. The treatment is preferably effected orally, for example using pharmaceutical capsules, in doses containing one third of the daily dosage three times a day.

According to one preferred feature of the invention, the γ-linolenic acid or functional derivative thereof is administered together with a daily dosage of from 5mg to 3g of linoleic acid or a functional derivative thereof. Convenient functional derivatives include the $C_1$–$C_4$ alkyl (e.g. methyl and ethyl) esters and the glycerides of linoleic acid.

At the present time known sources of oils having a high γ-linolenic acid content are few. One source currently available is the seed of the Evening Primrose or *Oenothera biennis L.* the oil extract therefrom containing γ-linolenic acid and linoleic acid in the form of their triglycerides. Another source of γ-linolenic acid is the seed of *Borago Officinalis* which provides a richer source of γ-linolenic acid with smaller amounts of linoleic acid. Recent studies on fungi which can be cultivated by fermentation promise another commercial source.

The oil extract may be administered as such or it may be fractionated to yield an oily composition containing γ-linolenic acid and linoleic acid as the only fatty acid components, the γ-linolenic acid content being for example as high as 90%.

The treatment in accordance with the invention can be effected using pharmaceutical compositions in dosage unit form containing as active ingredient γ-linolenic acid itself or a functional derivative thereof, or an oil extract containing the γ-linolenic acid or functional derivative thereof, in association with an acceptable pharmaceutical vehicle therefor.

The pharmaceutical compositions will conveniently contain linoleic acid or a functional derivatives thereof together with the γ-linolenic acid component as active ingredient.

The term "pharmaceutical vehicle" is used herein to embrace the wide variety of modes of presentation which may be adopted with the active materials, and is qualified with the term "pharmaceutical" so as to exclude any possibility that the nature of the compositions, considered of course in relation to the route by which they are intended to be administered, could be harmful rather than beneficial.

Without detraction from the generality of the foregoing definition of the term "pharmaceutical vehicle", it can be stated for purposes of guidance that, subject always to the exclusion of ingredients of a toxic or otherwise noxious nature, or which would interfere with the pharmacological actions of the materials, the term may be regarded as having the following particular meanings in relation to the modes of administration identified below.

a. So far as oral administration is concerned, the term means the ingestible coherent solid excipient of a tablet or coated tablet, the ingestible container of a capsule or cachet, the ingestible and usually flavoured pulverulent solid carrier of a powder or granules, or the again usually flavoured ingestible liquid medium of a syrup or elixir. In general, since the active materials are normally liquid, the vehicle will be suitable for the presentation of a liquid and will be a diluting, dispersing, surface active, suspending, binding, lubricating, flavouring, preserving, thickening or emulsifying agent.

b. So far as administration by injection is concerned, the term means a sterile injectable liquid solution or suspension medium, preferably isotonic with the body fluids encountered in the vicinity of the intended site of injection. In general, the vehicle will be an anti-oxidant, buffer, bacteriostat, solute which renders the composition isotonic with said body fluid, suspending agent or thickening agent. Moreover, an extemporaneous injection solution or suspension may be prepared from sterile powders, granules or tablets.

Whilst the modes of presentation just listed represent those most likely to be employed, they do not necessarily exhaust the possibilities. However, the preferred method of administering the active materials is orally, a particularly preferred mode of presentation at present being in the form of capsules.

Conveniently the compositions are prepared by admixture.

Powders for oral administration may be prepared by forming a homogeneous dispersion of the active material in an ingestible pulverulent solid carrier, either by mixing and grinding it with the carrier, or by first pasting the pulverised carrier with the active material itself, or with a solution of the material, and then drying. Examples of suitable inert materials for inclusion as the carrier are calcium carbonate, calcium silicate, talc, calcium sulphate, kaolin, hard paraffin, beeswax, kieselguhr and magneisum stearate. These can be replaced or supplemented by binders such as sugar, starch, lactose and pectin. Flavour can be imparted to the powder by incorporation of sugar and/or aromatic substances such as soluble cocoa powder. When the pulverulent solid carrier is pasted with a solution of the desired active material, the solvents employed may include water, alcohol, chloroform and sorbitol, as may be appropriate.

Tablets may be prepared by compressing the powders just described into coherent shapes of the appropriate size. To facilitate the manufacturing operation before compression the powders may advantageously be mixed also with binders and/or lubricants, such as starch, pectin, gelatin, gum arabic, methylcellulose, carboxyl-methyl cellulose (preferably in the form of its sodium salt), talc, stearic acid and magnesium stearate, if these are not already present. The coherent tablets thus formed may be coated, for example with sugar to improve their appearance, taste and durability, and may, moreover, be scored to facilitate administration of smaller doses, if desired.

Capsules may be prepared by enclosing the active ingredient, if desired microencapsulated under a nitrogen atmosphere, within a casing or sheath formed of gelatin, glycogelatin or other suitable material. The nature of this material is chosen in relation to the point in the digestive system at which it is desired to release the active material. It is conveniently either of melting point less than body temperature, or soluble in gastric juices, thus, for example, at pH's of 2 or less, or 9 or more.

Syrups and elixirs may be prepared by dissolving or suspending the active material in aqueous liquid media, which may contain a sweetening agent such as sugar, saccharin or a polyhydric alcohol like glycerol or sorbitol, or another flavouring agent, such as alcohol, chloroform, citrates, or of course both. In the case of suspensions, surface-active agents such as glyceryl monostearate, aluminium monostearate and/or ethyl oleate may be incorporated to maintain the suspension, and solubilizing agents may be employed in solutions, together with suitable co-solvents such as alcohols, chloroform and trichloroethylene, if these are not already present. The thixotropy and viscosity of the liquid medium may be adjusted by the inclusion of appropriate amounts of pectin, gelatin, gum tragacanth, carboxy-methyl-cellulose, or agar-agar. Colourants may also be incorporated.

Injectable preparations may be prepared by forming solutions and/or suspensions in any of the usual sterile media, which may be oily or aqueous. Injectable solutions of hydrolysed oil may be prepared using albumin to solubilise the free acid. Preferably the preparations are rendered isotonic with the body fluids, and adjusted to the desired viscosity.

Advantageously a preservative such as α-tocopherol is incorporated into the preparation. α-Tocopherol in a concentration of about 0.1% by weight has been found suitable for the purpose.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired. Thus preferred daily dosages of active ingredient for the treatment of multiple sclerosis are from 25mg to 3g of γ-linolenic acid or functional derivative thereof and, when present, from 25mg to 3g of linoleic acid or functional derivative thereof. On the other hand, when used to provide an immunosuppressive effect in organ and tissue transplants it will generally be advantageous to administer after the operation a daily dosage of from 25mg to 3g of γ-linolenic acid or functional derivative thereof and, when present, from 25mg to 3g of linoleic acid or functional derivative thereof. Pre-operative treatment advantageously comprises administration of a daily dosage of 25mg to 3g of γ-linolenic acid or functional derivative thereof over a prolonged period. Alternatively in urgent cases pre-operative treatment may comprise administration of a large dose (e.g. 0.25 to 3g) of γ-linolenic acid or a functional derivative thereof.

In general compositions for parenteral administration may conveniently be provided in the form of micronised emulsions containing 5 to 20% γ-linolenic acid in dosage units of 10ml. Compositions for oral administration are conveniently provided in the form of capsules containing the oil as such or in microencapsulated form in a unit dose of 250mg to 1g again of 5–20% γ-linolenic cid.

Tests have been conducted to assess the immuno-suppressive effect and the effect on arachidonic acid levels of administering γ-linolenic acid in accordance with the present invention.

For example in vitro studies of the inhibition of the interaction of normal lymphocytes with thyroid (F1) antigen have been effected by means of the Macrophage Electrophoretic Mobility (MEM) Test [viz. E. A. Caspary and E. J. Field, *British Medical Journal*, 1971, 2, 613]. In these experiments, the test subjects were first given a heavy animal fat meal. This was followed by administration of a dose of the test material. At certain intervals after administration of the oil serum samples were taken and subjected to the MEM test. For each test material, the experiment was repeated several times with administration of different dosages. The test materials were as follows:

1. Naudicelle Oil — an oil extract from the seeds of *Oenothera biennis L.* containing 74% linoleate and 8.6% γ-linolenate (Test Material A)
2. A fraction of the oil extract used in 1) containing 90% pure γ-linolenate with the remaining 10% being linoleate (Test Material B)
3. Pure linoleic acid (Test Material C) A blank experiment was also carried out to determine the base-line position.

The % reduction in lymphocyte-antigen reaction has been plotted against dosage in the accompanying drawing from which the strong inhibitory effect of the γ-linolenic acid-containing test materials can readily be seen.

The relative effects of oral supplements of γ-linolenic acid-containing oil and safflower oil on arachidonic acid deficiency has been assessed for example in the following tests carried out on rats. Weanling rats of the Hooded Lister Strain were maintained on a fat free diet of the following composition.

| Constituent | % by weight |
| --- | --- |
| Casein | 16 |
| Sucrose | 74 |
| Cellulose | 4 |
| Salts | 4 |

After 12 weeks on the above diet 4 animals were killed for determination of the base line fatty acid composition. The remaining animals were split into two groups each consisting of 16 animals. One group was then orally supplemented with 100 mg/rat/day of safflower oil and the other with 100 mg/rat/day of the oil extract from seeds of *Oenothera biennis L.* containing 8.3% γ-linolenic acid and 73% linoleic acid (Naudicelle Oil).

The animals in each group were then killed, 4 at a time about 3,5,9 and 12 supplementation. Liver, heart, adrenal and red cells from each animal were analysed for arachidonic acid content.

In all tissues the level of arachidonic acid was elevated more quickly and reached higher levels at the end of supplementation in animals given the γ-linolenic aid-containing oil extract than in those given safflower oil which contains about the same linoleic acid concentration but no γ-linolenic acid.

The pharmacological results point to the usefulness of the treatment in accordance with the invention for the control or prophylaxis of neurological disorders such as multiple sclerosis and in the fields of organ and other tissue transplants.

Whilst the invention has been described above with reference to the use of γ-linolenic acid and its functional derivatives it has furthermore been found that dihomo-γ-linolenic acid has a similar activity and can in accordance with the present invention be used instead of or together with γ-linolenic acid. Thus the present invention further provides a method of providing an immunosuppressive effect in the control or prophylaxis of neurological disorders and in organ and tissue transplants which comprises administering a daily dosage of from 5mg to 3g of dihomo-γ-linolenic acid or a functional derivative thereof, for example the $C_1$–$C_4$ alkyl (e.g. methyl and ethyl) esters and the glycerides.

The invention is further illustrated by the following Examples which are not intended to limit the invention in any manner.

EXAMPLES

Pharmaceutical compositions containing a unit dose of the oil extract from the seeds of *Cenothera biennis, L.* are prepared by encapsulation of the natural oil in soft gelatin capsules manufactured by known methods.

The oil is extracted from the seeds by one of the conventional methods of extraction such as cold pressure, screw pressure after partially cooking the seed or solvent extraction [see J. Chem. Soc., 1961, 2728].

Oil extracts from these seeds generally contain from 7–26% γ-linolenic acid and from 70–72% linoleic acid predominantly in the form of the triglyceride esters. Typical analytical results are as follows:

| | |
| --- | --- |
| Specific gravity | 0.923 |
| Iodine value | 154 |
| Ester value | 191 |
| Non-saponifiable matter | 1.52% |
| Acid value | 1.4 |

Fractionation shows a yield of 97.0% of fatty acids in the form of methyl esters.

| Proportions of methyl esters: | |
| --- | --- |
| Palmitate | 6.14% |
| Stearate | 1.58% |
| Oleate | 10.15% |
| Linoleate | 72.60% |
| Γ-Linolenate | 8.87% |

If the γ-linolenic and linoleic acid contents are below the desired levels, they are adjusted by adding the required quantities from a reserve stock of the acids obtained from previous seed stocks giving higher yields, or from concentrates of the acids in the form of the methyl or ethyl esters extracted from previous batches of oil, or produced by chemical synthesis.

A suitable preservative such as α-tocopherol is added to the oil in a concentration of 0.1%.

EXAMPLE 1

Gelatin capsules containing 350mg of linoleate and 50mg of γ-linolenate prepared as described above are administered at a rate of 4-6 capsules per day to patients suffering from multiple sclerosis. The capsules are taken in a dosage of 1 or 2 capsules three times daily, morning, mid-day and evening, one and a half hours after meals.

EXAMPLE 2

Gelatin capsules having the following unit dose formulation were administered to multiple sclerosis sufferers analogously to Example 1:

| | |
|---|---|
| linoleate | 175mg |
| Γ-linolenate | 100mg |

EXAMPLE 3

Gelatin capsules containing the following unit dose formulation were administered to multiple sclerosis patients analogously to Example 1:

| | |
|---|---|
| linoleate | 75mg |
| Γ-linolenate | 150mg |

EXAMPLE 4

Gelatin capsules containing a unit dose of an oil extract from the seeds of *Borago Officinalis* prepared as described above are administered to kidney transplant patients. Each unit dose contains 48mg of linoleate and 432mg of γ-linolenate. One capsule is administered every 4 hours over a 12 hour period prior to the operation. Following the operation a maintainance dose of 2capsules per day is administered, morning, mid-day and evening one and a half hours afer meals for a period of 6 months.

EXAMPLE 5

Prior to operation pure γ-linolenic acid is administered to a kidney transplant patient in a daily dose of 1.75g as two separate doses morning and evening. The γ-linoleic acid is administered intraveneously as a sterile micronised emulsion. Following the transplant the treatment is continued for a period of 6 months, the γ-linolenic acid being administered orally 3 times per day with capsules as in Example 4.

The above Examples may be repeated substituting dihomo-γ-linolenic acid in like doses for the γ-linolenic acid.

What I claim is:

1. A method of providing an immuno-suppressive effect in a patient suffering from multiple sclerosis which comprises administering to said patient a daily dosage of from 25mg to 3g of at least one compound selected from the group consisting of γ-linolenic acid, dihomo-γ-linolenic acid, $C_1$-$C_4$ alkyl esters of γ-linolenic and dihomo-γ-linolenic acids and glyceride esters of γ-linolenic and dihomo-γ-linolenic acids.

2. A method as claimed in claim 1 wherein a dose containing one third of the daily dosage is administered three times a day.

3. A method as claimed in claim 2 wherein the treatment is effected orally using capsules containing a unit dose of 250mg to 1g of an oil extract containing 5-20 wt.% γ-linolenic acid.

4. A method as claimed in claim 3 wherein the oil is microencapsulated within the capsules.

5. A method as claimed in claim 2 wherein the treatment is effected parenterally using a micronised emulsion containing 5-20% γ-linolenic acid in a unit dose of 10ml.

6. A method of providing an immuno-suppressive effect in a patient suffering from multiple sclerosis which comprises administering to said patient a daily dosage of from 25mg to 3g of at least one compound selected from the group consisting of γ-linolenic acid, dihomo-γ-linolenic acid, $C_1$-$C_4$ alkyl esters of γ-linolenic and dihomo-γ-linolenic acids and glyceride esters of γ-linolenic and dihomo-γ-linolenic acids, together with a daily dosage of from 5mg to 3g of linoleic acid, $C_1$-$C_4$ alkyl esters or glyceride esters thereof.

7. A method as claimed in claim 6 wherein an oil extract from the seeds of *Oenothera biennis L.* which contains both γ-linolenic acid or ester and linoleic acid or ester is administered.

8. A method as claimed in claim 7 wherein the oil extract is a fraction containing linoleic and γ-linolenic acids as the only fatty acid components.

* * * * *